(12) United States Patent
Morf et al.

(10) Patent No.: US 12,145,004 B2
(45) Date of Patent: Nov. 19, 2024

(54) SYSTEMS AND METHODS FOR DETECTING AND/OR MEASURING MOTION AND POSITION ASSOCIATED WITH A PATIENT

(71) Applicant: Varian Medical Systems International AG, Cham (CH)

(72) Inventors: Daniel Morf, Buch am Irchel (CH); Reto Filiberti, Steinhausen (CH); Patrik Kunz, Baden (CH)

(73) Assignee: Siemens Healthineers International AG, Steinhausen (CH)

( * ) Notice: Subject to any disclaimer, the term of this patent is extended or adjusted under 35 U.S.C. 154(b) by 1485 days.

(21) Appl. No.: 15/473,495

(22) Filed: Mar. 29, 2017

(65) Prior Publication Data

US 2017/0281976 A1  Oct. 5, 2017

Related U.S. Application Data

(60) Provisional application No. 62/316,743, filed on Apr. 1, 2016.

(51) Int. Cl.
*A61N 5/10* (2006.01)
*A61B 5/00* (2006.01)
(Continued)

(52) U.S. Cl.
CPC .......... *A61N 5/1049* (2013.01); *A61B 5/0816* (2013.01); *A61B 5/113* (2013.01);
(Continued)

(58) Field of Classification Search
CPC .. A61N 5/1049; A61N 5/1048; A61N 5/1064; A61N 5/1065; A61N 5/1067;
(Continued)

(56) References Cited

U.S. PATENT DOCUMENTS 3,803,539 A   4/1974  Mcmaster
4,122,427 A   10/1978 Karsh
(Continued)

FOREIGN PATENT DOCUMENTS

EP  3245943 A1 * 11/2017
GB  2464345 A  *  4/2010 ........... A61B 5/1135

OTHER PUBLICATIONS

Machine translation of EP 3245943 A1. Retrieved from worldwide.espacenet.com on Oct. 24, 2022. (Year: 2022).*
(Continued)

*Primary Examiner* — Benjamin S Melhus
*Assistant Examiner* — Samuel C Kim
(74) *Attorney, Agent, or Firm* — Harness, Dickey & Pierce, P.L.C.

(57) ABSTRACT

An apparatus for patient position or motion monitoring includes: an energy source configured to emit energy from a first location to a second location, or vice versa, wherein the second location that is moveable relative to the first location in response to a movement by a patient; and a processing unit coupled to receive an input that is based on the emitted energy, and to determine a characteristic associated with the patient based on the input.

35 Claims, 6 Drawing Sheets

(51) Int. Cl.
*A61B 5/08* (2006.01)
*A61B 5/113* (2006.01)
*A61B 8/08* (2006.01)
*A61B 90/00* (2016.01)

(52) U.S. Cl.
CPC .............. *A61B 5/7285* (2013.01); *A61B 8/08* (2013.01); *A61B 5/486* (2013.01); *A61B 2090/3929* (2016.02); *A61B 2090/3945* (2016.02); *A61B 2090/3979* (2016.02); *A61N 2005/105* (2013.01); *A61N 2005/1051* (2013.01); *A61N 2005/1058* (2013.01); *A61N 2005/1059* (2013.01)

(58) Field of Classification Search
CPC ...... A61N 2005/105; A61N 2005/1051; A61N 2005/1058; A61N 2005/1059; A61N 2005/1054; A61B 5/0816; A61B 5/113; A61B 5/7285; A61B 5/486; A61B 5/1128; A61B 5/1135; A61B 5/1127; A61B 5/7282; A61B 8/08; A61B 2090/3929; A61B 2090/3945; A61B 2090/3979
See application file for complete search history.

(56) References Cited

U.S. PATENT DOCUMENTS

| | | | |
|---|---|---|---|
| 4,197,856 A | | 4/1980 | Northrop |
| 4,696,307 A | | 9/1987 | Montgieux |
| 5,220,922 A | | 6/1993 | Barany |
| 6,110,112 A | * | 8/2000 | Heywang-Koebrunner ................ A61B 17/3403 600/461 |
| 8,068,051 B1 | | 11/2011 | Osterweil |
| 9,155,911 B1 | * | 10/2015 | Balakin .................. A61N 5/107 |
| 9,731,148 B2 | * | 8/2017 | Olivera .................... A61B 6/08 |
| 11,234,768 B1 | * | 2/2022 | Henderson ............. A61B 90/37 |
| 2003/0188757 A1 | * | 10/2003 | Yanof .................. A61B 5/1135 600/427 |
| 2004/0210155 A1 | * | 10/2004 | Takemura ................ A61B 5/00 702/159 |
| 2006/0079763 A1 | * | 4/2006 | Jeung ..................... A61B 6/032 600/428 |
| 2006/0100509 A1 | * | 5/2006 | Wright ................. A61N 5/1049 600/426 |
| 2007/0055144 A1 | * | 3/2007 | Neustadter ............ A61B 90/39 600/425 |
| 2007/0183041 A1 | * | 8/2007 | McCloy ................. A61B 34/20 359/515 |
| 2009/0082687 A1 | * | 3/2009 | Onishi ................. A61B 5/1135 600/534 |
| 2010/0106165 A1 | * | 4/2010 | Jacob ................... A61B 6/0421 128/845 |
| 2011/0060215 A1 | * | 3/2011 | Tupin, Jr. ............. A61B 5/1075 600/407 |
| 2012/0008745 A1 | * | 1/2012 | Stahl .................... A61N 5/1047 378/65 |
| 2013/0338525 A1 | * | 12/2013 | Allen ................... A61B 5/0062 600/534 |
| 2013/0345718 A1 | * | 12/2013 | Crawford ............... A61B 10/02 606/130 |
| 2014/0088433 A1 | * | 3/2014 | Shan .................... A61B 5/1128 600/473 |
| 2014/0194793 A1 | * | 7/2014 | Nakata .................. G01S 13/825 601/48 |
| 2014/0343344 A1 | * | 11/2014 | Saunders ............. A61B 6/4291 600/1 |
| 2014/0343421 A1 | * | 11/2014 | Kim ......................... A61N 7/02 601/3 |
| 2015/0223733 A1 | * | 8/2015 | Al-Alusi ............... A61B 5/1112 600/479 |
| 2016/0166197 A1 | * | 6/2016 | Venkatraman ......... A61B 5/021 600/301 |
| 2016/0302871 A1 | * | 10/2016 | Gregerson ........... A61B 5/0036 |
| 2016/0310083 A1 | * | 10/2016 | Wang .................... A61B 5/318 |
| 2016/0345867 A1 | * | 12/2016 | Aoki .................... A61B 5/1127 |
| 2017/0014648 A1 | * | 1/2017 | Mostafavi .............. A61B 6/102 |
| 2017/0127980 A1 | * | 5/2017 | Rabb .................... A61B 5/4806 |
| 2017/0215772 A1 | * | 8/2017 | Garn .................... A61B 5/0806 |
| 2017/0311840 A1 | * | 11/2017 | Suematsu ............ A61B 5/0816 |

OTHER PUBLICATIONS

Saw CB, Brandner E, Selvaraj R, Chen H, Saiful Huq M, Heron DE. A review on the clinical implementation of respiratory-gated radiation therapy. Biomed Imaging Interv J. Jan. 2007;3(1):e40. doi: 10.2349/biij.3.1.e40. Epub Jan. 1, 2007. PMID: 21614265; PMCID: PMC3097646. (Year: 2007).*

M. M. Saad, et al., "High-Accuracy Reference-Free Ultrasonic Location Estimation", IEEE Transactions on Instrumentation and Measurement, vol. 61, No. 6, Jun. 2012, 10 pages.

Mike Hazas, et al., "A Novel Broadband Ultrasonic Location System", in Proceedings of UbiComp 2002: Fourth International Conference on Ubiquitous Computing, Lecture Notes in Computer Science, vol. 2498, Sep. 2002, 17 pages.

Mike Hazas, et al., "Broadband Ultrasonic Location Systems for Improved Indoor Positioning", IEEE Transactions on Mobile Computing, vol. 5, No. 5, May 2006, 12 pages.

Hexamite, "Hx11", www.hexamite.com, http://hexamite.com/hx11.htm, Nov. 5, 2013, 28 pages.

* cited by examiner

SYSTEMS AND METHODS FOR DETECTING AND/OR MEASURING MOTION AND POSITION ASSOCIATED WITH A PATIENT

RELATED APPLICATION DATA

This application claims priority to and the benefit of U.S. Provisional Patent Application No. 62/316,743, filed on Apr. 1, 2016, pending. The entire disclosure of the above application is expressly incorporated by reference herein.

FIELD

The field of the application relates to systems and methods for detecting and/or measuring patient motion, such as respiratory motion.

BACKGROUND

Radiation therapy involves medical procedures that selectively expose certain areas of a human body, such as cancerous tumors, to high doses of radiation. The intent of the radiation therapy is to irradiate the targeted biological tissue such that the harmful tissue is destroyed. During a radiation therapy, a radiation source may be rotated around a patient to deliver radiation from different angles at target region inside the patient. The radiation source may be mounted on an arm or a ring gantry. In certain radiation therapy, the patient support supporting the patient may also be moved.

During radiation therapy, it may be desirable to measure respiratory motion of the patient. For example, the measured respiratory motion of the patient may be used to gate a delivery of radiation.

In other types of therapy that may or may not involve use of radiation, it may also be desirable to measure respiratory motion of a patient. For examples, in ultrasound therapy or proton therapy, sometimes it may also be desirable to use a measured respiratory motion to gate a delivery of therapeutic energy.

Furthermore, in some cases, it may also be desirable to measure respiratory motion of a patient during a diagnostic procedure. For example, in a 4D computed tomography (CT) imaging process, the respiratory motion of the patient may be measured. The different phases of the breathing of the patient may then be correlated with different projection images. Projection images belonging to the same breathing phase may then be used in an image reconstruction process to reconstruct a three dimensional image.

Applicant of the subject disclosure determines that it may be desirable to provide a new system and method for measuring respiratory motion of a patient.

SUMMARY

An apparatus for patient position or motion monitoring includes: an energy source configured to emit energy from a first location to a second location, or vice versa, wherein the second location that is moveable relative to the first location in response to a movement by a patient; and a processing unit coupled to receive an input that is based on the emitted energy, and to determine a characteristic associated with the patient based on the input.

Optionally, the energy source is configured to emit energy from the first location to the second location, not from the second location to the first location.

Optionally, the apparatus further includes a receiver for operation with the energy source.

Optionally, the receiver is at the second location, and is configured to receive the energy directly from the energy source.

Optionally, the receiver is configured to receive reflected energy from the second location.

Optionally, the receiver is closer to the first location than the second location.

Optionally, the receiver and the energy source are integrated into a single device.

Optionally, the energy source is configured to emit energy from the second location to the first location, not from the first location to the second location.

Optionally, the apparatus further includes a receiver for operation with the energy source.

Optionally, the receiver is at the first location, and is configured to receive the energy directly from the energy source.

Optionally, the receiver is configured to receive reflected energy from the first location.

Optionally, the processing unit is configured to determine the characteristic of the patient based on time-of-flight technique.

Optionally, the processing unit is configured to determine the characteristic of the patient based on observation of geometric pattern or based on input from laser interferometer(s).

Optionally, the characteristic comprises a breathing characteristic, and the processing unit is configured to determine the breathing characteristic of the patient.

Optionally, the breathing characteristic comprises a breathing amplitude, a breathing phase, a period of a respiratory cycle, a breathing pattern, or any combination of the foregoing.

Optionally, the apparatus further includes a receiver for operation with the energy source.

Optionally, the apparatus further includes a mounting device configured to mount the energy source or the receiver to a patient support.

Optionally, the apparatus further includes a mounting device configured to mount the energy source or the receiver to a gantry of another component of a radiation machine.

Optionally, the gantry comprises a ring gantry.

Optionally, the apparatus further includes a mounting device configured to mount the energy source or the receiver to a ceiling or a wall.

Optionally, the energy source or the receiver has an operative position that is above a torso, a belly, or a head, of the patient.

Optionally, the apparatus further includes a screen for displaying an image for viewing by the patient.

Optionally, the image is for instructing the patient to control a breathing of the patient.

Optionally, the apparatus further includes a support structure, wherein the energy source or the receiver is moveably mounted to the support structure, and wherein the screen is also mounted to the support structure.

Optionally, the apparatus further includes a support structure, wherein the energy source or the receiver is rotatably mounted to the support structure.

Optionally, the energy source or the receiver is also slidably mounted to the support structure.

Optionally, the support structure comprises a telescopic arm.

Optionally, the energy source comprises an ultrasound device, a laser device, an infrared device, or a light device configured to emit ultraviolet light or visible light.

Optionally, the apparatus further includes an additional energy source configured to emit energy.

Optionally, the apparatus further includes one or more receivers for operation with the energy source, or for operation with the energy source and the additional energy source.

Optionally, the additional energy source is configured to emit the energy for measuring a distance between the energy source and an object that is fixed in position with respect to the energy source.

Optionally, the object comprises a patient support.

Optionally, the apparatus further includes one or more accelerometer(s) for determining an orientation of the energy source with respect to one or more axes.

Optionally, the apparatus further includes a measurement device configured to determine, or to provide information for determining, a distance between the first and second locations.

Optionally, the measurement device comprises a time-of-flight measurement device.

Optionally, the apparatus further includes a fiducial, wherein the energy source is configured to emit energy towards the fiducial.

Optionally, the fiducial comprises a marker, a marker plate, or a marker block.

Optionally, the marker comprises an active marker.

A medical system includes the apparatus described herein, and a medical device.

Optionally, the medical device comprises an imaging device.

Optionally, the medical device comprises a treatment device.

Optionally, the medical device comprises a ring gantry.

A method for determining a breathing of a patient, includes: emitting energy from an energy source from a first location to a second location, or vice versa, wherein the second location is moveable in response to a movement by the patient; generating an input by an energy receiver; receiving, by a processing unit, the input from the receiver; and determining, using the processing unit, a characteristic of the patient based on the input from the receiver.

Optionally, the characteristic comprises a breathing characteristic of the patient.

Optionally, the breathing characteristic comprises a breathing amplitude, a breathing phase, a period of a respiratory cycle, a breathing pattern, or any combination of the foregoing.

Optionally, the energy source or the receiver is above a torso, a belly, or a head, of the patient.

Optionally, the energy source or the receiver is mounted to a patient support, a gantry, a ceiling, or a wall.

Optionally, the energy source comprises an ultrasound device, a laser device, an infrared device, or a light device configured to emit ultraviolet light or visible light.

Optionally, the method further includes displaying an image on a screen for viewing by the patient.

Optionally, the image is for instructing the patient to control a breathing of the patient.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
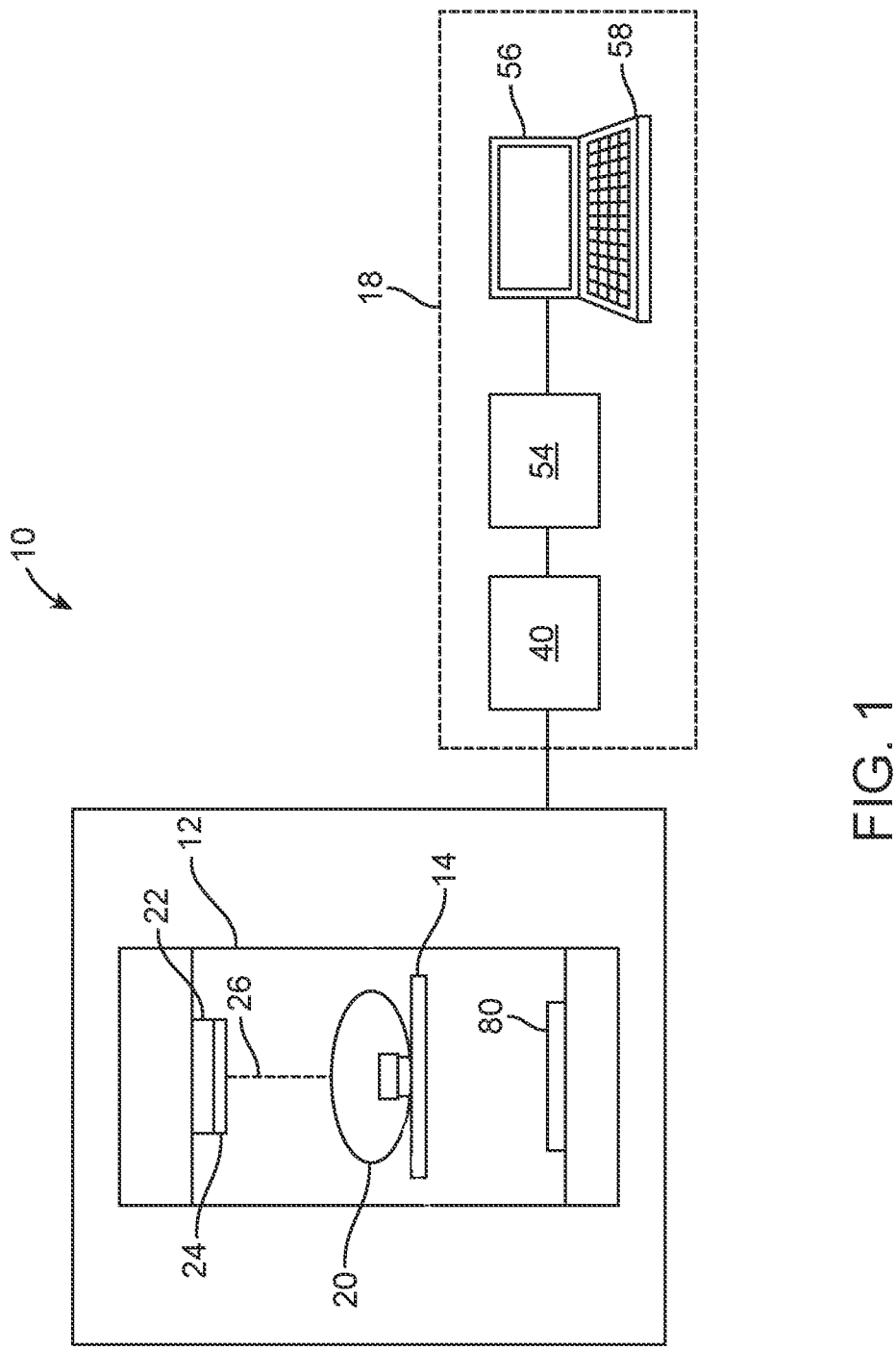
FIG. 1 illustrates a radiation treatment system.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a radiation treatment system 10. The system 10 includes an arm gantry 12, a patient support 14 for supporting a patient 20, and a control system 18 for controlling an operation of the gantry 12 and delivery of radiation. The system 10 also includes a radiation source 22 that projects a beam 26 of radiation towards the patient 20 while the patient 20 is supported on support 14, and a collimator system 24 for changing a cross sectional shape of the radiation beam 26. The radiation source 22 may be configured to generate a cone beam, a fan beam, or other types of radiation beams in different embodiments. Also, in other embodiments, the source 22 may be configured to generate proton beam as a form of radiation for treatment purpose. Also, in other embodiments, the system 10 may have other form and/or configuration. For example, in other embodiments, instead of an arm gantry 12, the system 10 may have a ring gantry 12.

In the illustrated embodiments, the radiation source 22 is a treatment radiation source for providing treatment energy. In other embodiments, in addition to being a treatment radiation source, the radiation source 22 can also be a diagnostic radiation source for providing diagnostic energy for imaging purpose. In such cases, the system 10 will include an imager, such as the imager 80, located at an operative position relative to the source 22 (e.g., under the support 14). In further embodiments, the radiation source 22 may be a treatment radiation source for providing treatment energy, wherein the treatment energy may be used to obtain images. In such cases, in order to obtain imaging using treatment energies, the imager 80 is configured to generate images in response to radiation having treatment energies (e.g., MV imager). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 22 is able to generate X-ray radiation at a plurality of photon energy levels within a range anywhere between approximately 10 keV and approximately 20 MeV. In further embodiments, the radiation source 22 can be a diagnostic radiation source. In such cases, the system 10 may be a diagnostic system with one or more moving parts. In the illustrated embodiments, the radiation source 22 is carried by the arm gantry 12. Alternatively, the radiation source 22 may be located within a bore (e.g., coupled to a ring gantry).

In the illustrated embodiments, the control system 18 includes a processing unit 54, such as a processor, coupled to a control 40. The control system 18 may also include a monitor 56 for displaying data and an input device 58, such as a keyboard or a mouse, for inputting data. The operation of the radiation source 22 and the gantry 12 are controlled by the control 40, which provides power and timing signals to the radiation source 22, and controls a rotational speed and position of the gantry 12, based on signals received from the processing unit 54. Although the control 40 is shown as a separate component from the gantry 12 and the processing unit 54, in alternative embodiments, the control 40 can be a part of the gantry 12 or the processing unit 54.

In some embodiments, the system 10 may be a treatment system configured to deliver treatment radiation beam towards the patient 20 at different gantry angles. During a treatment procedure, the source 22 rotates around the patient 20 and delivers treatment radiation beam from different gantry angles towards the patient 20. While the source 22 is at different gantry angles, the collimator 24 is operated to change the shape of the beam to correspond with a shape of the target tissue structure. For example, the collimator 24 may be operated so that the shape of the beam is similar to a cross sectional shape of the target tissue structure. In another example, the collimator 24 may be operated so that different portions of the target tissue structure receive different amount of radiation (as in an IMRT procedure).

Figure 2:
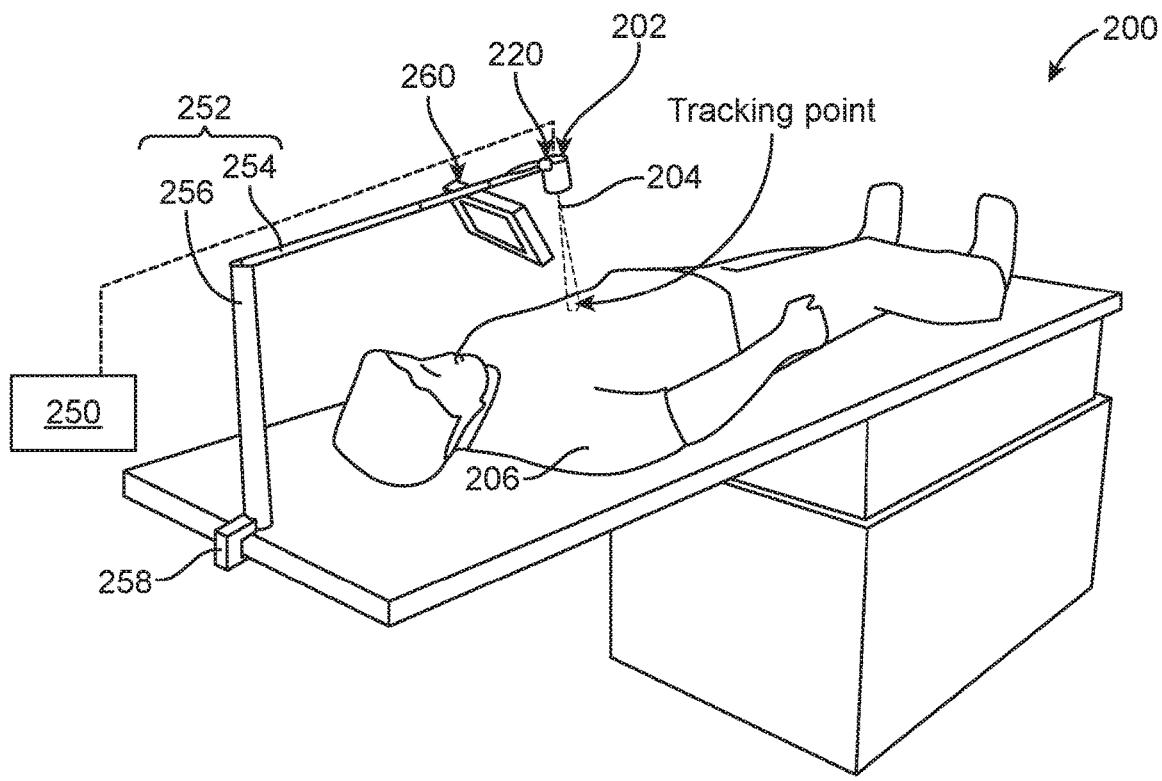
FIG. 2 illustrates a respiratory motion measuring apparatus.

FIG. 2 illustrates a respiratory motion measuring apparatus 200. The respiratory motion measuring apparatus 200 may be used with the radiation treatment system 10, or with other medical devices or systems. The apparatus 200 includes an energy device 202 configured to emit energy 204 towards a torso of a patient 206; and a processing unit 250 coupled to the energy device 202, wherein the processing unit 250 is configured to receive an input from the energy device 202, and determine a breathing characteristic of the patient 206. It should be noted that the processing unit 250 is not limited to being physically coupled to the energy device 202, and that the processing unit 250 may be communicatively coupled to the energy device 202 (e.g., wirelessly). Also, in some cases, the processing unit 250 and the energy device 202 may be in different respective rooms. In other cases, they may be in the same room.

The energy device 202 is configured to provide energy towards the patient 206, and sense the energy after the energy has been reflected from the patient 206. The energy device 202 may include an energy source configured to provide the energy 204 and/or an energy receiver to receive (e.g., detect) the energy 204 after it has been reflected from the patient 206. In some cases, the energy source and the energy receiver may be integrated into a single component. In other cases, the energy source and the energy receiver may be separate components. By means of non-limiting examples, the energy device 202 may comprise an ultrasound device configured to provide ultrasound energy and/or to sense reflected ultrasound energy, a laser device configured to provide laser and/or to sense reflected laser, an infrared device configured to provide infrared energy and/or to sense reflected infrared energy, a light device configured to emit ultraviolet light or visible light, and/or to sense reflected ultraviolet light or visible light, or any of other types of energy device configured to provide and/or sense energy.

In some cases, the energy 204 from the energy device 202 may be delivered to the patient (e.g., to the skin of the patient, to a cloth being worn by the patient, or to a blanket covering the patient). In other cases, the respiratory motion measuring apparatus 200 may include a fiducial that is configured to be coupled to the torso of the patient. In such cases, the energy device 202 is configured to emit the energy 204 towards the fiducial and/or to sense the energy 204 after it has been reflected from the fiducial. By means of non-limiting examples, the fiducial may include one or more marker(s), a marker plate, or a marker block. The marker(s) may be passive marker(s) and/or active marker(s), e.g., marker(s) that sends out a signal, such as infrared, visible light, ultraviolet ray, ultrasound, etc. In some cases, the cloth being worn by the patient 206 or a blanket covering the patient 206 may be considered to be a part of the patient, or the fiducial itself. Providing a fiducial coupled to the patient may be advantageous because it allows the respiratory motion measuring apparatus 200 to detect and track the measurement reference so that the same location with respect to the patient is always used for obtaining the measurement. Also, in other cases, the energy 204 from the energy device 202 may be delivered to a belly, or to a fiducial coupled to the belly, of the patient, thereby using the belly directly or indirectly as a measurement reference.

It should be noted that the respiratory motion measuring apparatus 200 is not limited to having only one energy device 202. In other cases, the respiratory motion measuring apparatus 200 may include one or more additional energy device(s) configured to emit energy or energies towards the torso of the patient, or to different parts of the patient. The additional energy device(s) may provide additional measurement points to monitor patient movements. The multiple measurements may provide redundancy for tracking a certain part (e.g., torso) of the patient 206, or may track multiple different parts of the patient 206.

In the illustrated embodiments, the energy device 202 of the respiratory motion measuring apparatus 200 is configured to function as a measurement device configured to determine, or to provide information for determining, a distance from a torso of the patient. For example, in some cases, the energy device 202 itself may include a timer that measures the time it takes for the energy 204 to reach the patient or a fiducial, and to travel back to the receiver of the energy device 202. The energy device 202 may provide the time information to the processing unit 250, which then determines a distance between the energy device 202 (e.g., the receiver in the energy device 202) and the patient 206 (or a fiducial coupled to the patient 206) based on a speed of travel of the energy 204. In other cases, the energy device 202 may include a processing unit to determine the distance based on the time information.

Figure 3:
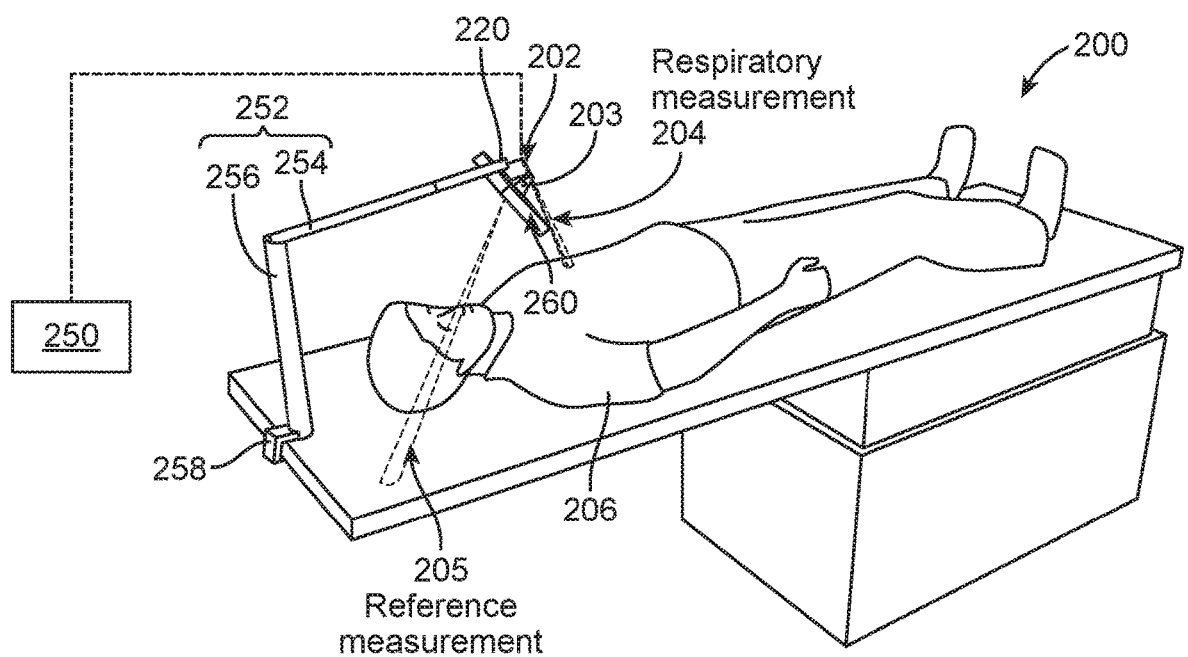
FIG. 3 illustrates a respiratory motion measuring apparatus.

In other embodiments, the respiratory motion measuring apparatus 200 may include another measurement device (e.g., a time-of-flight measurement device) configured to determine, or to provide information for determining, a distance from a fixed object. In particular, the respiratory motion measuring apparatus 200 may optionally further include a second energy device 203 configured to provide energy 205 for measuring a distance relative to a fixed object, e.g., a surface of the patient support (FIG. 3). The second energy device 203 is communicatively coupled to the processing unit 250 using a cable or a wireless system. The second energy device 203 may include an energy source configured to provide the energy 205 and/or an energy receiver to receive (e.g., detect) the energy 205 after it has been reflected from the object. In some cases, the energy source and the energy receiver may be integrated into a single component. In other cases, the energy source and the energy receiver may be separate components. By means of non-limiting examples, the second energy device 203 may comprise an ultrasound device configured to provide ultrasound energy and/or to sense reflected ultrasound energy, a laser device configured to provide laser and/or to sense reflected laser, an infrared device configured to provide infrared energy and/or to sense reflected infrared energy, a light device configured to emit ultraviolet light or visible light, and/or to sense reflected ultraviolet light or visible light, or any of other types of energy device configured to provide and/or sense energy. Although only one additional energy device 203 is shown in FIG. 3, in other embodiments, there may be more than one additional energy device 203. For example, in other cases, there may be a first additional energy device 203 and a second additional energy device 203 configured to provide respective energies to fixed objects. The additional energy devices 203 may be configured to receive reflected energies from the respective fixed objects, and distances from the fixed objects can then be determined by the processing unit 250 using time-of-flight technique.

Returning to FIG. 2, in some cases, the processing unit 250 may be configured to determine the breathing characteristic of the patient 206. In some embodiments, the energy device 202 provides time information to the processing unit 250 regarding a time it takes for the energy 204 to travel from the energy source 202 to the patient 206 (or a fiducial coupled to the patient 206), and then back to the energy device 202. In such cases, the processing unit 250 includes a distance determination module configured to receive the time information and information regarding a speed of travel for the energy 204, and calculate a distance between the energy device 202 and the patient 206 (or a fiducial that is coupled to the patient 206) based on time-of-flight technique. In other cases, the energy device 202 may itself determine the distance, and transmit the distance to the processing unit 250. In either case, after obtaining the distance, the processing unit 250 may determine one or more breathing characteristic of the patient 206. By means of non-limiting examples, the breathing characteristic may be one or more breathing amplitude(s), one or more breathing phase(s), a period of a respiratory cycle, a breathing pattern, or any combination of the foregoing. It should be noted that the embodiments described herein are not limited to using time-of-flight technique to determine the distance between the energy device 202 and the patient 206, and that other techniques may be used in other embodiments. For example, in other embodiments, observation of geometric pattern or laser interferometer(s) may be used.

In some cases, the processing unit 250 may include a breathing amplitude determination module configured to determine breathing amplitudes. In some cases, the distance information obtained by the processing unit 250 may be used as the breathing amplitudes. In other cases, the breathing amplitude determination module may perform scaling, averaging, normalization, or any combination of the foregoing, using the distance values to determine breathing amplitudes. The breathing amplitudes may be stored in a non-transitory medium for later use. In addition, or alternatively, the breathing amplitudes may be displayed on a screen for presentation to a user.

Figure 5:
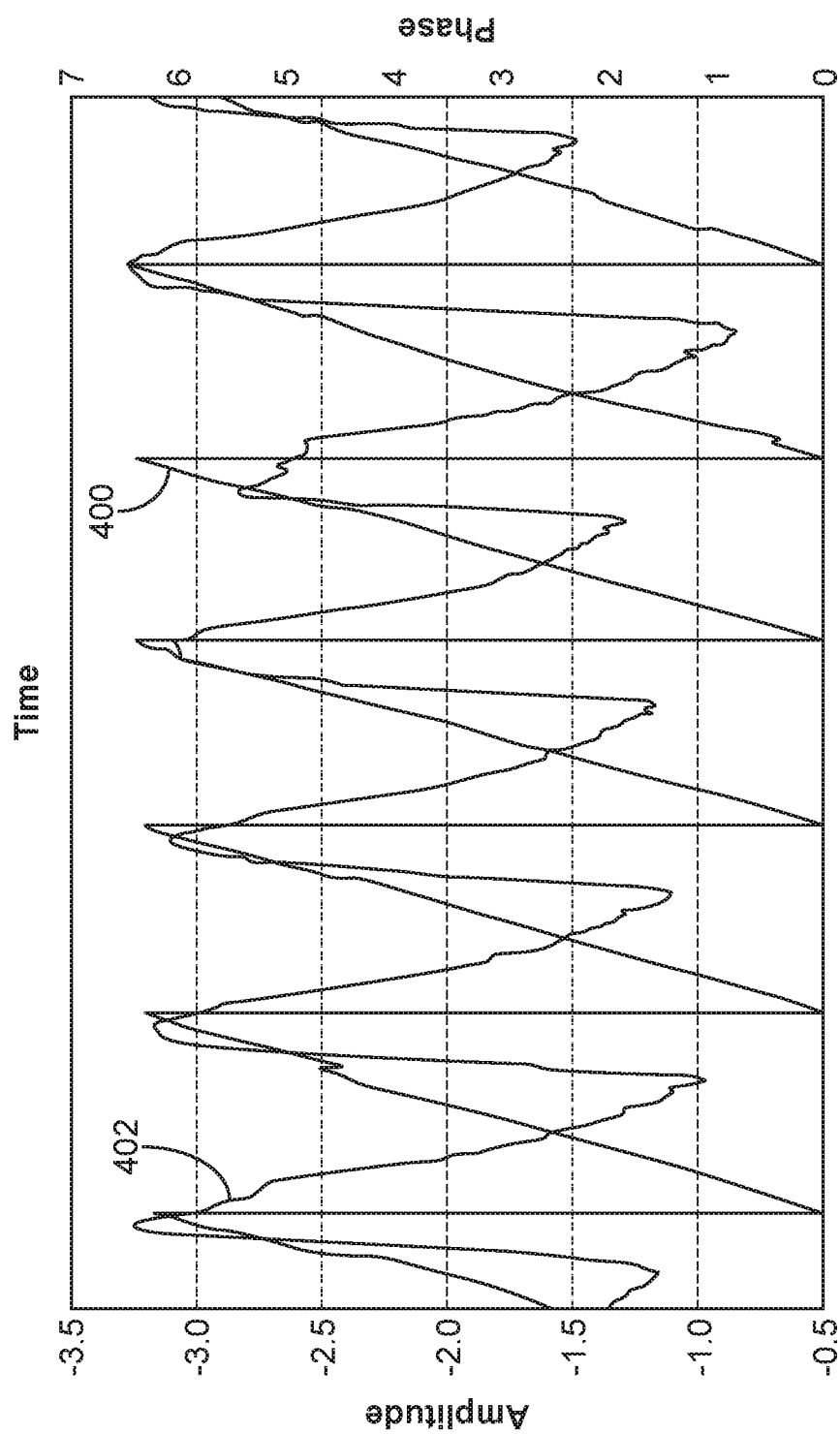
FIG. 5 illustrates an amplitude diagram aligned with a phase diagram.

Also, in some cases, the processing unit 250 may include a breathing phase determination module configured to determine breathing phases. In particular, by determining a plurality of positions of the patient's torso or fiducial over a period of time, the processing unit 250 can be configured to obtain a plurality of phase points that correspond to different levels of completeness of a breathing cycle at various time points. For example, a phase value may have a value from 0° to 360°, with 0° representing a beginning of a respiratory cycle, and 360° representing an end of the respiratory cycle. FIG. 5 illustrates an example of a phase diagram 400 that is aligned with a corresponding amplitude/position diagram 402. Amplitude diagram 402 includes positional points of the patient (e.g., torso) or fiducial determined using embodiments of the technique described herein. Each point in the amplitude diagram 402 represents a position of a bodily part or fiducial at a certain point in time. In the illustrated example, a phase value of 0° (and 360°) represents a peak of an inhale state, and the phase value varies linearly between 0° and 360° in a physiological cycle. As shown in the diagram, for each point in the amplitude diagram 402 at certain point in time, a corresponding phase value at the same point in time may be obtained. Thus, for each breathing amplitude, the processing unit 250 can determine the corresponding phase of the respiratory cycle.

The breathing phases may be stored in a non-transitory medium for later use. In addition, or alternatively, the breathing phases may be displayed on a screen for presentation to a user.

In some embodiments, the determined phase values may be used to gate an execution of a procedure, such as, to gate an application of a treatment radiation to the patient 206 for treatment, or to gate an application of an imaging radiation to the patient 206 for imaging purpose. In further embodiments, the phase values may be used to perform tracking of a target region while IMRT is being performed.

In other embodiments, the determined phase values may be used to gate a binning of image data, either in real time while the image data is being obtained, or after the image data has been obtained. For example, in a 4D-CT imaging session, the respiratory motion measuring apparatus 200 may be used to determine the positions of the patient's torso representing different breathing amplitudes of the patient 206, while a CT machine generates different projection images of the patient 206 at different respective gantry angles. The positions of the patient's torso may be used to determine breathing phases for association with different projection images. For example, different projection images generated at different gantry angles but belonging to a same phase range (phase bin) may be associated together. The associated projection images may then be used to construct a volumetric CT image for that particular phase bin. Also, in some embodiments, different volumetric CT images for different phase bins may be constructed (e.g., using the processing unit 250 or another processor), and the sequence of volumetric CT images may be displayed in a video.

Furthermore, in some embodiments, the processing unit 250 may include a breathing period determination module configured to determine a breathing period of a patient. In one technique, the breathing period determination module of the processing unit 250 may be configured to determine two maximum amplitudes in the breathing amplitude graph, and then determine the period between the two maximum amplitudes. The period may then be used as the period of the breathing cycle. Alternatively, the breathing period determination module of the processing unit 250 may be configured to determine two minimum amplitudes in the breathing amplitude graph, and then determine the period between the two minimum amplitudes. The period may then be used as the period of the breathing cycle. In further embodiments, the breathing period determination module may be configured to determine a duration between a first phase value (e.g., 0°) and a second phase value (e.g., 360°), and use the duration as the breathing period. The breathing period may be stored in a non-transitory medium for later use. In addition, or alternatively, the breathing period may be displayed on a screen for presentation to a user.

In further embodiments, the processing unit 250 may include a breathing pattern determination module configured to determine a breathing pattern of the patient 206. In one implementation, the processing unit 250 is configured to receive a plurality of breathing amplitude data, and store the breathing amplitude data with their corresponding time points in a non-transitory medium. In some cases, the breathing amplitude data and their corresponding time points form a breathing pattern, which may be used as a reference breathing pattern for later use. For example, after the reference breathing pattern has been established, the respiratory motion measuring apparatus 200 may continue to monitor a breathing of the patient 206. As the breathing of the patient 206 is being monitored, the respiratory motion measuring apparatus 200 continues to generate breathing amplitude data for processing by the processing unit 250. The processing unit 250 may use the breathing amplitude data to determine a current breathing pattern of the patient 206. The processing unit 250 may also compare the current breathing pattern with the reference breathing pattern to determine if the patient 206 is breathing regularly or not. In some cases, if the processing unit 250 detects a deviation from periodicity for the breathing of the patient 206, the processing unit 250 may then generate a signal to stop a medical procedure, and/or to warn a technician.

In some cases, the breathing pattern may be stored in a non-transitory medium for later use. In addition, or alternatively, the breathing pattern may be displayed on a screen for presentation to a user.

Returning to FIG. 2, in some embodiments, the processing unit 250 may be coupled to the energy device 202 using a cable. In other embodiments, the processing unit 250 may be coupled to the energy device 202 using a wireless system. In such cases, the energy device 202 may include a first wireless device, and the processing unit 250 may include a second wireless device for communication with the first wireless device.

As shown in the figure, the respiratory motion measuring apparatus 200 further includes a support structure 252, wherein the energy device 202 is moveably mounted to the support structure 252. In the illustrated embodiments, the support structure 252 includes a telescopic arm 254 and a vertical support 256. The telescopic arm 254 allows the energy device 202 to translate relative to the vertical support 256 of the support structure 252. Accordingly, the energy device 202 is slidably mounted to a part of the support structure 252. Also, in the illustrated embodiments, the energy device 202 is rotatably mounted to one end of the telescopic arm 254 via a moveable connector 220, e.g., a hinge or a ball joint. In some cases, the energy device 202 is coupled to the support structure 252 such that the energy device 202 may translate in three degrees of freedom (e.g., along X-axis, Y-axis, and Z-axis that are orthogonal to each other), and/or rotate in three degrees of freedom (e.g., rotate about X-axis, Y-axis, and Z-axis).

It should be noted that the support structure 252 is not limited to the example shown in the figure, and that the support structure 252 may have other configurations in other embodiments. For example, in other cases, the support structure 252 may have a different form. Also, in other cases, the support structure 252 may not include any telescopic arm. In addition, in other cases, instead of mounting above the head of the patient 206, the support structure 252 may be mounted to a side of the patient support or to a bottom part of the patient support supporting the patient's feet. Accordingly, the telescopic arm 254 does not need to extend above the patient's head, and may extend above the patient's shoulder, above the bottom torso of the patient, etc. Furthermore, in other cases, instead of mounting to the patient support, the support structure 252 may be configured to be mounted to another object, such as a gantry of a radiation machine (e.g., CT machine, radiation treatment machine, etc.), a ceiling, a wall, etc. Furthermore, in other embodiments, the support structure 252 may not be needed. Instead, the energy device 202 may be mounted directly to an object, such as a patient support, a gantry, an arm, a ceiling, etc.

As shown in the figure, the energy device 202 has an operative position that is above the torso of the patient 206. In other embodiments, the energy device 202 may have an operative position that is located at other places with respect to the patient 206. For example, the energy device 202 may be located above a head of the patient 206, or above the feet of the patient 206.

In addition, as shown in the figure, the respiratory motion measuring apparatus 200 further includes a mounting device 258 configured to mount the energy device 202 with respect to the patient support. In the illustrated example, the mounting device 258 is a clamp located at a bottom end of the vertical support 256 configured to detachably mount the vertical support 256 to the patient support. In other cases, the mounting device 258 may include a snap-fit connector, one or more screws, and/or other type of connectors for securing the respiratory motion measuring apparatus 200 relative to an object, such as the patient support, a gantry, a ceiling, a wall, etc.

Also, as shown in the figure, the respiratory motion measuring apparatus 200 further includes a screen 260 for displaying an image for viewing by the patient 206. The screen 260 is mounted to the telescopic arm 254 of the support 252. In other cases, the screen 260 may be mounted to the vertical support 256, or to another support structure. In some cases, the image may be for instructing the patient 206 to control a breathing of the patient 206. For example, the image in the screen 260 may display a command for instructing the patient 206 to hold breath, to inhale, to exhale, or any combination of the foregoing. In some embodiments, the screen 260 may provide an animation (e.g., in a form of a game) for allowing the patient 206 to play, wherein an object in the image may be controlled by the patient's breathing. In the animation, the patient 206 may be instructed to control the object using his/her breathing so that the position of the object coincides with one or more target objects in the screen 260. By means of non-limiting examples, the one or more target objects may include a first horizontal bar representing a desired inhale level, a second horizontal bar representing a desired exhale level, or both. Also, in other examples, the one or more target objects may include multiple target objects that are moving in the screen 260 (e.g., blocks moving linearly across the screen 260).

Figure 4:
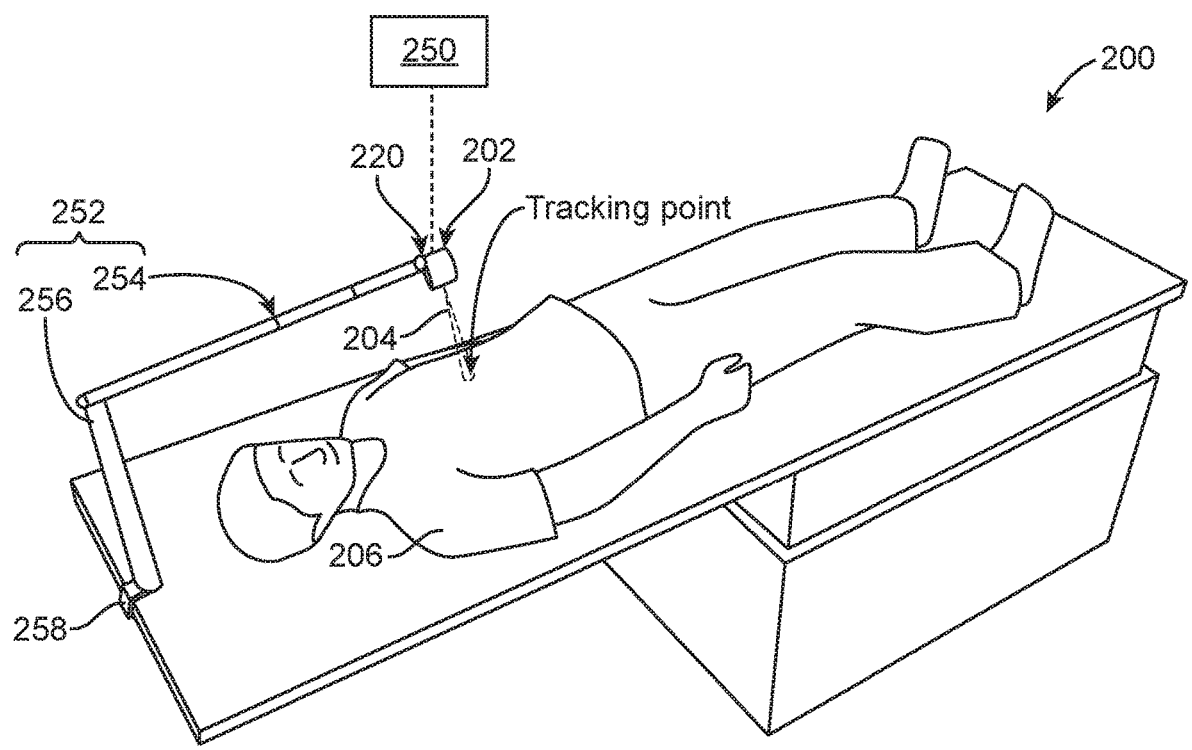
FIG. 4 illustrates a respiratory motion measuring apparatus.

In other embodiments, the screen 260 is optional, and the respiratory motion measuring apparatus 200 may not include the screen 260 (FIG. 4).

During use of the respiratory motion measuring apparatus 200, the energy device 202 is first positioned at its intended operative position relative to the patient 206. In the illustrated example, the energy device 202 is placed above the torso of the patient 206 aiming downward towards the torso of the patient 206. The energy device 202 then emits the energy 204 towards the patient 206. The energy 204 reflected from the patient 206 and travels back towards the energy device 202. A receiver in the energy device 202 receives (e.g., detects) the reflected energy, and the energy device 202 or the processing unit 250 may then determine a time it takes for the energy 204 to travel to the patient 206 and to reflect back to the receiver. Based on the time information, the energy device 202 and/or the processing unit 250 may then use time-of-flight technique to determine a distance between the energy device 202 and the torso of the patient 206. As the patient 206 breathes, the chest of the patient 206 moves up and down. Accordingly, the distance between the energy device 202 and the moving torso varies during a breathing cycle. The energy device 202 is configured to provide the energy 204 and to receive the reflected energy at a frequency that is much higher than a frequency of the patient's breathing. Thus, as the patient 206 breathes, the respiratory motion measuring apparatus 200 generates multiple positional data representing different positions of the torso of the patient 206 during to breathing. It should be noted that the respiratory motion apparatus 200 is not limited to using time-of-flight technique to determine the distance between the energy device 202 and the torso of the patient 206, and that other techniques may be used in other embodiments. For example, in other embodiments, observation of geometric pattern or laser interferometer(s) may be used.

The respiratory motion measuring apparatus 200 and the method 500 are advantageous because they require no or minimal calibration effort, and they do not require use of any camera system. Also, in the embodiments in which the respiratory motion measuring apparatus 200 is mounted to the patient support, the use of the apparatus 200 is independent of the position of the patient support. In addition, in some cases, the apparatus 200 may allow for couch kick. Furthermore, in the embodiments in which the energy device 202 delivers energy 204 directly to the patient 206 (i.e., without use of any marker block), use of the apparatus 200 provides biocompatibility and cleaning advantageous because there is no marker block that touches the patient 206.

Figure 6:
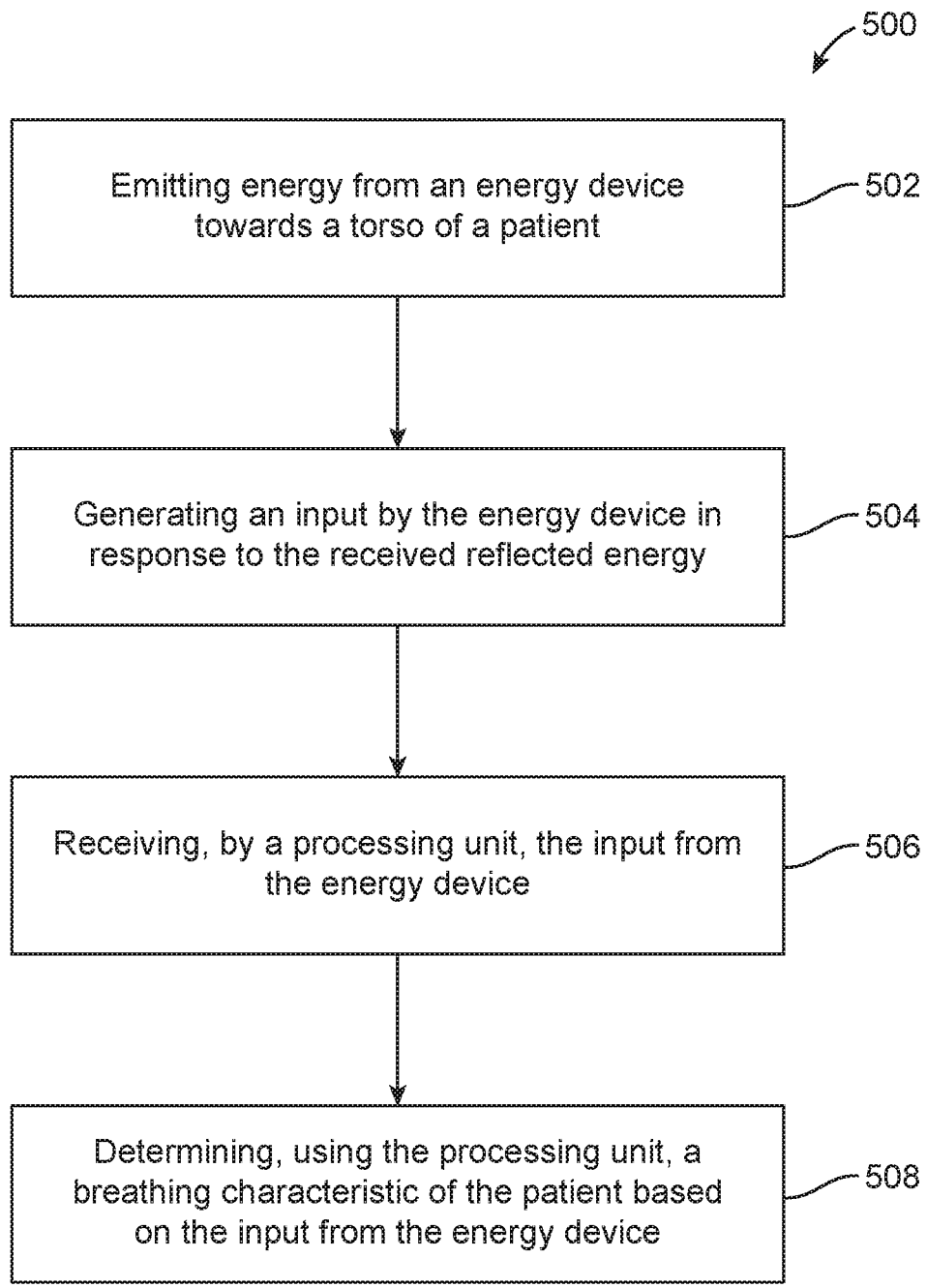
FIG. 6 illustrates a method for determining a breathing characteristic of a patient.

FIG. 6 illustrates a method 500 for determining a breathing characteristic of a patient. The method 500 includes emitting energy from an energy device towards a torso of a patient (item 502) receiving reflected energy by the energy device. The method 500 also includes generating an input by the energy device in response to the received reflected energy (item 504). The method 500 further includes receiving, by a processing unit, the input from the energy device (item 506). In addition, the method 500 further includes determining, using the processing unit, a breathing characteristic of the patient based on the input from the energy device (item 508).

Optionally, the breathing characteristic of the patient is determined based on time-of-flight technique.

Optionally, the breathing characteristic comprises a breathing amplitude, a breathing phase, a period of a respiratory cycle, or a breathing pattern.

Optionally, the energy device is above the torso.

Optionally, the energy device is mounted to a patient support, a gantry, a ceiling, or a wall.

Optionally, the energy device comprises an ultrasound device, a laser device, an infrared device, or a light device configured to emit ultraviolet light or visible light.

Optionally, the method further includes displaying an image on a screen for viewing by the patient.

Optionally, the image is for instructing the patient to control a breathing of the patient.

It should be noted that the apparatus and method described herein are not limited to monitoring patient movement, and that they can be applied for monitoring a position of a patient. For example, the apparatus described herein may be used to determine whether the patient did move or not during a procedure (e.g., imaging procedure, and/or a treatment procedure).

Also, in other embodiments, instead of using the torso as a reference point, other features may be used as reference point. For example, a marker or a marker block placed on the belly may be used as a reference point. In another example, a head of the patient may be used as a reference point.

Furthermore, in any of the embodiments described herein, the apparatus may further include one or more accelerometer(s) for sensing an orientation of the energy device 202 with respect to one or more axes. The accelerometer(s) may be incorporated inside a housing of the energy device 202, or may be coupled to the energy device 202, so that an orientation of the energy device 202 can be sensed by the accelerometer(s). During use of the energy device 202, the energy device 202 may not be aiming vertically towards a torso of the patient. For example, the energy device 202 may be aiming at a non-vertical direction towards the torso of the patient. The accelerometer(s) is advantageous because it can sense the orientation of the energy device 202, which indicates the direction of aiming by the energy device 202. The sensed orientation may be transmitted to the processing unit (e.g., by wire, or wirelessly). Based on the sensed orientation of the energy device 202, and time of flight information, the processing unit may then calculate a vertical distance between the patient and a reference location (which vertical distance may be the vertical component of the distance between the energy device 202 and the patient along the aiming direction). In other embodiments, instead of using accelerometer(s), the apparatus may use other types of orientation sensor(s) for sensing an orientation of the energy device 202.

It should be noted that the processing unit is not limited to determining a vertical distance, and that the processing unit may be configured to determine any distance along any axis in other embodiments.

As discussed, the energy device 202 includes an energy source for emitting energy, and a receiver for receiving (e.g., detecting) reflected energy, wherein both the energy source and the receiver are fixedly coupled to a same reference location. In other embodiments, the energy source and the receiver of the energy device 202 may be at different respective locations. Accordingly, it should be noted that the term "device" or "energy device" is not limited to a single item/object at a single location, and may refer to multiple components/items that are at different respective locations. For example, in some cases, the receiver may be placed at or coupled directly or indirectly to the patient, while the energy source is fixedly mounted to a reference location (e.g., a support, the patient support, or a part of a medical machine). Thus, movement of the patient will cause the receiver to move correspondingly relative to the energy source. During use, the energy source emits energy towards the patient. The processing unit keeps track of the time at which energy is emitted. When the receiver receives (e.g., detects) the emitted energy, it transmits to the processing unit the time at which the energy is received. Based on the time of energy emission, and the time of energy reception, the processing unit can then determine a distance between the energy source and the receiver. In other embodiments, the energy source may be placed at or coupled directly or indirectly to the patient, while the receiver is fixedly mounted to a reference location. In such cases, movement of the patient will cause the energy source to move correspondingly relative to the receiver.

In further embodiments, both the energy source and the receiver may be placed at or coupled directly or indirectly to the patient. During use, the energy source of the energy device 202 emits energy towards a reference location (that is fixed with respect to some coordinate system), which may be an object that is fixedly coupled directly or indirectly to the patient support or to a component of a medical machine. The energy is reflected from the reference location, and travels back towards the receiver. Based on the time it takes for the emitted energy to travel from the energy source and to come back to the receiver, the processing unit can then determine the distance between the energy device 202 and the reference location.

Also, in any of the embodiments described herein, there may be multiple energy sources operating with one receiver, or one energy source operating with multiple receivers, or multiple energy sources operating with multiple receivers.

Specialized Processing System

Figure 7:
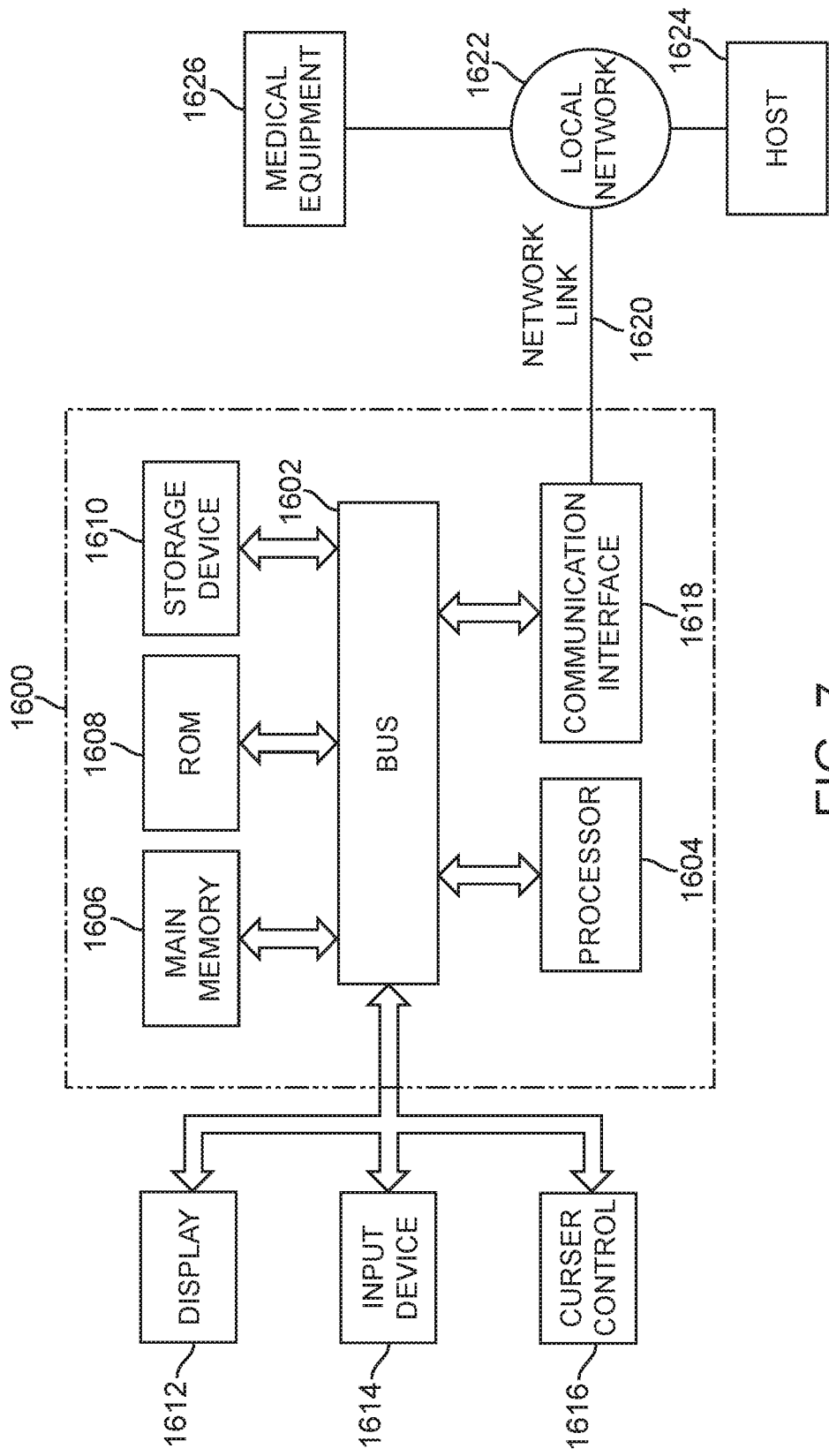
FIG. 7 illustrates a specialized processing system with which embodiments described herein may be implemented.

FIG. 7 is a block diagram illustrating an embodiment of a specialized processing system 1600 that can be used to implement various embodiments described herein. For example, the processing system 1600 may be configured to implement the method of FIG. 6 in accordance with some embodiments. Also, in some embodiments, the processing system 1600 may be used to implement the processing unit 54 of FIG. 1, the processing unit 250 of FIG. 2, 3, or 4, or any processing unit described herein.

Processing system 1600 includes a bus 1602 or other communication mechanism for communicating information, and a processor 1604 coupled with the bus 1602 for processing information. The processor 1604 may be an example of the processor 54 of FIG. 1, or an example of any processor described herein. The processing system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processing system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processing system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processing system 1600 can be used to perform various functions described herein. According to some embodiments, such use is provided by processing system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another computer-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "computer-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

In the above embodiments, the respiratory motion measuring apparatus 200 has been described with reference to it being used with a radiation machine in a radiation procedure (e.g., CT imaging, radiation treatment, etc.). However, it should be noted that the respiratory motion measuring apparatus 200 and the method 500 may be used with other types of machine and in other procedures. For example, the respiratory motion measuring apparatus 200 may be used with a proton machine in a proton treatment procedure, with an ultrasound machine in an ultrasound imaging and/or treatment procedure. Also, in other embodiments, the respiratory motion measuring apparatus 200 may be used in a data collection process that does not involve any treatment or medical imaging. For example, in other cases, the method 500 may be performed to determine a plurality of positional data representing breathing amplitudes of a patient. The positional data may be stored in a non-transitory medium for later use. For example, the positional data may be used later in a treatment process.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. An apparatus for patient position or motion monitoring, the apparatus comprising:
 a first energy source configured to emit a first energy from a first location to a second location, wherein a distance between the first location and the second location is variable in response to a movement by a patient, the first energy source including an accelerometer configured to sense an orientation of the first energy source;
 a second energy source configured to emit a second energy to a surface of the patient support;
 a processor configured to
  determine a characteristic associated with the patient using a time-of-flight technique based on the first energy reflected from the patient and the orientation of the first energy source, the characteristic comprising a breathing characteristic including a breathing phase including breathing phase values,
  determine a distance between the second energy source and the surface of the patient support based on the second energy reflected from the surface of the patient support to the second energy source, and
  gate an application of a treatment to the patient based on the breathing phase values; and
 a support structure having a mounting device, a vertical support and a telescopic arm, the support structure configured to:
  mount to a patient support via the mounting device, the patient support including longitudinal edges extending along a length of the patient support and transverse edges extending perpendicular to the longitudinal edges, the mounting device configured to be removably coupled to one of the transverse edges of the patient support, and
  maintain the first energy source and the second energy source at a fixed position with respect to the patient support;
 wherein the processor is configured to repeatedly determine the characteristic associated with the patient based on the first energy reflected from the patient while the support structure maintains the first energy source at the fixed position with respect to the patient support; and
 wherein, when mounted, the vertical support extends vertically from the mounting device and the telescopic arm extends from an end of the vertical support over the patient support.

2. The apparatus of claim 1, further comprising a receiver configured to operate with the first energy source.

3. The apparatus of claim 2, wherein the receiver is configured to receive the first energy reflected from the patient at the second location.

4. The apparatus of claim 3, wherein the receiver is closer to the first location than the second location.

5. The apparatus of claim 4, wherein the receiver and the first energy source are integrated into a single device.

6. The apparatus of claim 2, wherein the first energy source or the receiver has an operative position that is above a torso, a belly, or a head of the patient.

7. The apparatus of claim 2, wherein at least one of the first energy source, the second energy source, or the receiver is moveably mounted to the support structure.

8. The apparatus of claim 1, wherein the breathing characteristic further includes one or more of a breathing amplitude, a period of a respiratory cycle, or a breathing pattern.

9. The apparatus of claim 1, further comprising a screen configured to display an image designed to be presented to the patient, wherein the screen is mounted in front of the patient for viewing by the patient, and wherein the screen is mounted to the support structure that is configured to maintain the first energy source at the fixed position with respect to the patient support.

10. The apparatus of claim 9, wherein the image is for instructing the patient to control a breathing of the patient.

11. The apparatus of claim 1, wherein the first energy source comprises an ultrasound device, a laser device, an infrared device, or a light device configured to emit ultraviolet light or visible light.

12. The apparatus of claim 1, further comprising one or more receivers configured to operate with the first energy source, or configured to operate with the first energy source and the second energy source.

13. The apparatus of claim 1, wherein the accelerometer is configured to determine the orientation of the first energy source with respect to one or more axes.

14. The apparatus of claim 1, further comprising a fiducial, wherein the first energy source is configured to emit energy towards the fiducial.

15. The apparatus of claim 14, wherein the fiducial comprises a marker, a marker plate, or a marker block.

16. The apparatus of claim 15, wherein the marker comprises an active marker.

17. A medical system comprising the apparatus of claim 1, and a medical device.

18. The medical system of claim 17, wherein the apparatus comprises an imaging device.

19. The medical system of claim 17, wherein the medical device comprises a radiation source configured to deliver treatment energy.

20. The apparatus of claim 1, wherein the processor is configured to determine breathing amplitudes or breathing phases based on time of flight data.

21. The apparatus of claim 1, wherein a mounting location of the mounting device is at a head-end of the patient support, and wherein the telescopic arm extends over the head-end of the patient support.

22. The apparatus of claim 1, wherein the first energy source is attached to an end of the telescopic arm via a movable connector.

23. The apparatus of claim 1, wherein the telescopic arm extends over a head-end of the patient support.

24. An apparatus for patient position or motion monitoring, the apparatus comprising:
a first energy source configured to emit a first energy from a first location to a second location, wherein a distance between the first location and the second location is variable in response to a movement by a patient, the first energy source including an accelerometer configured to sense an orientation of the first energy source;
a second energy source configured to emit a second energy to a surface of the patient support;
a processor configured to
receive an input that is based on the emitted first energy,
determine a characteristic associated with the patient based on the emitted first energy and the orientation of the first energy source the characteristic comprising a breathing characteristic including a breathing phase including breathing phase values,
determine a distance between the second energy source and the surface of the patient support based on the second energy reflected from the surface of the patient support to the second energy source, and
gate an application of a treatment to the patient based on the breathing phase values;
a receiver configured to operate with the first energy source to receive reflected energy after the emitted first energy is reflected from the patient; and
a support structure having a mounting device, a vertical support and a telescopic arm; wherein
the mounting device is configured to mount at least one of the first energy source, the second energy source, or the receiver to a patient support, the patient support including longitudinal edges extending along a length of the patient support and transverse edges extending perpendicular to the longitudinal edges, the mounting device configured to be removably coupled to one of the transverse edges of the patient support, and
when mounted, the vertical support extends vertically from the mounting device and the telescopic arm extends from an end of the vertical support over the patient support.

25. The apparatus of claim 24, wherein the processor is configured to repeatedly determine the characteristic associated with the patient based on the reflected energy after the emitted first energy is reflected from the patient while the at least one of the first energy source or the receiver is mounted to the patient support via the mounting device.

26. An apparatus for patient position or motion monitoring, the apparatus comprising:
a first energy source configured to emit a first energy from a first location to a second location, wherein a distance between the first location and the second location is variable in response to a movement by a patient, the first energy source including an accelerometer configured to sense an orientation of the first energy source;
a second energy source configured to emit a second energy to a surface of the patient support;
a processor configured to
receive an input that is based on the emitted first energy,
determine a characteristic associated with the patient based on the emitted first energy and the orientation of the first energy source, the characteristic comprising a breathing characteristic including a breathing phase including breathing phase values,
determine a distance between the second energy source and the surface of the patient support based on the second energy reflected from the surface of the patient support to the second energy source, and
gate an application of a treatment to the patient based on the breathing phase values;
a receiver configured to operate with the first energy source, wherein the receiver is configured to receive reflected energy after the emitted first energy is reflected from the patient; and
a support structure having a mounting device, a vertical support and a telescopic arm, the support structure configured to mount to a patient support via the mounting device, the patient support including longitudinal edges extending along a length of the patient support and transverse edges extending perpendicular to the longitudinal edges, the mounting device configured to be removably coupled to one of the transverse edges of the patient support;

wherein at least one of the first energy source, the second energy source, or the receiver is mounted to the support structure; and wherein, when mounted, the vertical support extends vertically from the mounting device and the telescopic arm extends from an end of the vertical support to support the at least one of the first energy source or the receiver above a torso, a belly, or a head of the patient while the patient is being supported on the patient support.

27. The apparatus of claim 26, wherein the first energy source or the receiver is at least one of rotatably or slidably mounted to the support structure.

28. The apparatus of claim 26, wherein the processor is configured to repeatedly determine the characteristic associated with the patient based on the reflected energy after the emitted first energy is reflected from the patient while the at least one of the first energy source or the receiver is mounted to the support structure.

29. A method for determining a breathing of a patient, the method comprising:

emitting a first energy from a first energy source from a first location to a second location, wherein a distance between the first location and the second location is variable in response to a movement by the patient;

emitting a second energy from a second energy source to a surface of the patient support;

generating an input by an energy receiver that is configured to receive reflected energy after the emitted first energy is reflected from the patient, the energy receiver including accelerometer configured to sense an orientation of the energy receiver;

receiving, by a processor, the input from the energy receiver;

determining, using the processor, a characteristic of the patient based on the input from the energy receiver and the orientation of the energy receiver, the characteristic comprising a breathing characteristic including a breathing phase including breathing phase values;

determining, using the processor, a distance between the second energy source and the surface of the patient support based on the second energy reflected from the surface of the patient support to the second energy source; and gating an application of a treatment to the patient based on the breathing phase values;

wherein at least one of the first energy source, the second energy source, or the energy receiver is mounted to a patient support via a mounting device, the patient support including longitudinal edges extending along a length of the patient support and transverse edges extending perpendicular to the longitudinal edges, the mounting device configured to be removably coupled to one of the transverse edges of the patient support; and wherein, when mounted, a vertical support extends vertically from the mounting device and a telescopic arm extends from an end of the vertical support over the patient support to maintain at least one of the first energy source, the second energy source, or the energy receiver at a location above the patient support.

30. The method of claim 29, wherein the breathing characteristic further comprises one or more of a breathing amplitude, a period of a respiratory cycle, or a breathing pattern.

31. The method of claim 29, wherein the first energy source or the energy receiver is above a torso, a belly, or a head of the patient.

32. The method of claim 29, wherein the first energy source comprises an ultrasound device, a laser device, an infrared device, or a light device configured to emit ultraviolet light or visible light.

33. The method of claim 29, further comprising displaying an image on a screen for viewing by the patient, wherein the screen is mounted in front of the patient for viewing by the patient.

34. The method of claim 33, wherein the image is for instructing the patient to control a breathing of the patient.

35. The method of claim 29, wherein the characteristic of the patient is repeatedly determined based on the reflected energy after the emitted first energy is reflected from the patient while the at least one of the first energy source or the energy receiver is mounted to the patient support.

* * * * *